United States Patent [19]  
Vanlerberghe et al.

[11] Patent Number: 4,678,665  
[45] Date of Patent: * Jul. 7, 1987

[54] POLYANIONIC COMPOUNDS DERIVED FROM AROMATIC ETHERS OF POLYGLYCEROLS

[75] Inventors: Guy Vanlerberghe, Claye Souilly; Henri Sebag, Paris, both of France

[73] Assignee: L'Oreal, Paris, France

[*] Notice: The portion of the term of this patent subsequent to May 26, 2004 has been disclaimed.

[21] Appl. No.: 637,025

[22] Filed: Aug. 2, 1984

[30] Foreign Application Priority Data

Aug. 2, 1983 [LU] Luxembourg .......................... 84 941

[51] Int. Cl.⁴ ...................... A61K 7/09; C07C 149/273
[52] U.S. Cl. ...................................... 424/72; 562/426; 562/429; 568/36; 568/37; 568/46; 568/47; 568/49; 568/50; 260/501.15; 424/47; 424/70; 424/71; 424/59; 8/405; 132/7
[58] Field of Search .................. 562/429, 426; 568/36, 568/37, 46, 47, 49, 50; 8/405; 132/7; 424/45, 59, 47, 71, 72; 260/501.15

[56] References Cited  
U.S. PATENT DOCUMENTS 3,998,948 12/1976 Vanlerberghe et al. ............... 568/37  
4,138,427 2/1979 Vanlerberghe et al. ............... 568/36

FOREIGN PATENT DOCUMENTS 2080303 2/1982 United Kingdom ................ 562/426  
2114988 9/1983 United Kingdom ................ 424/72

Primary Examiner—Natalie Trousof  
Assistant Examiner—Bruce D. Gray  
Attorney, Agent, or Firm—Cushman, Darby & Cushman

[57] ABSTRACT

Products of formula (I)

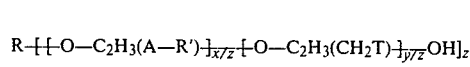

in which $R = C_{6-18}$ aromatic or alkylaromatic of valency z, $R' = H$, $C_{1-16}$ alkyl or phenyl, $A = CH_2$ or $CH_2$—O— and, in the latter case, $R' \neq H$, $x = 1-8$, $y = 1-20$, $z = 1-3$ and T denotes one or more anionic groups or a mixture of anionic groups and non-ionic groups are disclosed.

These compounds are prepared by the reaction of a phenol $R(OH)_z$ with an epoxide

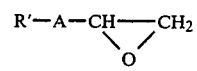

and an epihalogenohydrin

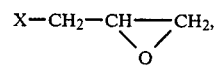

in which $X = Cl$ or Br, this being followed by replacement of X with one or more hydrophilic groups These compounds can be used as surface-active agents.

22 Claims, No Drawings

POLYANIONIC COMPOUNDS DERIVED FROM AROMATIC ETHERS OF POLYGLYCEROLS

The present invention relates to polyanionic compounds, a process for their preparation and their use in various compositions, especially cosmetic and pharmaceutical compositions.

Anionic surface-active agents obtained by reacting methyl or ethyl thioglycolate with polyhalogenated derivatives in the presence of sodium methylate are already known. The process for producing these surface-active agents uses thioglycolic acid esters, which have an unpleasant odour, are expensive and are not readily available on an industrial scale.

The process according to the present invention enables one to use smaller quantities of solvent, the reaction being carried out in an aqueous-alcoholic or even purely aqueous medium, in the presence of an alkali metal hydroxide.

The compounds obtained by this process have valuable surface-active properties, by themselves or in association with non-ionic or cationic surface-active agents, and generally produce a very rapid initial production of foam.

The compounds can be obtained by the telomerization of at least one alkylene oxide, alkyl glycidyl ether or aryl glycidyl ether and an epihalogenohydrin with a monohydric or polyhydric phenolic compound, and subsequent substitution of the halogen by a substituted alkylthio group.

The term "telomerization" denotes a polyaddition reaction of an epoxide with a compound possessing an active hydrogen atom. The compound possessing the active hydrogen is called a telogen, the epoxide compound is called a taxogen and the reaction product is called the telomer.

This invention provides products comprising a compound of formula (I):

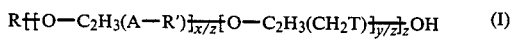

in which R denotes an aromatic or alkylaromatic radical of valency z, of 6 to 18 carbon atoms;

A denotes $CH_2$ or $CH_2$—O;

R' denotes H, an aliphatic radical, preferably an alkyl radical of 1 to 16 carbon atoms, or a phenyl radical with the proviso that R' cannot denote H if A denotes $CH_2$—O;

x denotes an integer or decimal number from 1 to 8;

y denotes an integer or decimal number from 1 to 20, preferably 3 to 15, x and y representing average statistical values;

z is an integer from 1 to 3; and

T denotes an anionic group, typically

—S—$CH_2$—COOM, —S—$CH_2$—$CH_2$—COOM,
$\downarrow$   $\downarrow$
(O)$_u$   (O)$_u$

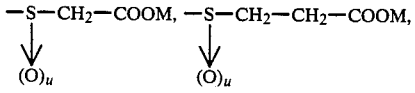

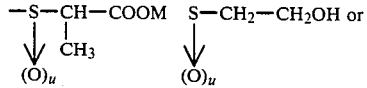

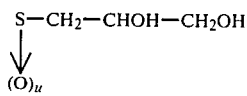

in which M denotes an alkali metal, preferably Na or K, an ammonium group or a substituted ammonium group, preferably corresponding to triethanolamine, 2-amino-2-methylpropan-1-ol or 2-amino-2-methylpropane-1,3-diol; and u denotes zero or 1, such that in the product, the groups —S—$CH_2$—$CH_2$OH and
$\downarrow$
(O)$_u$

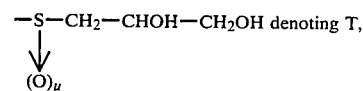

if present, are present in total amount of 1% to 50% by weight of the T groups.

It should be understood that, in formula (I), the units comprising the chain or chains may be present in any order, and the units will generally form rather statistical oligomers than block oligomers.

The group [O—$C_2H_3$(A—R')—] denotes both isomers:

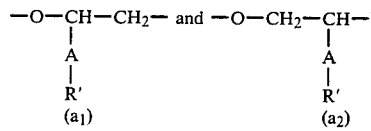

The group +O—$C_2H_3$($CH_2$T)+ denotes both isomers:

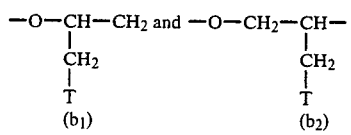

This invention also provides a process for the preparation of compounds of formula (I) comprising telomerizing, in a first step, one or more epoxides of formula (II):

R' and A having the same meanings as above, and an epihalogenohydrin of formula (III):

in which X denotes Cl or Br with a monohydric or polyhydric phenolic compound of formula:

R—(OH)$_z$ or a mixture of such compounds, R and z having the same meanings as above, to form a polyhalogenated intermediate of formula (IV):

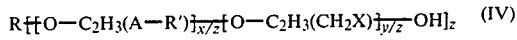

R, R', A, x, y, z and X having the same meanings as above and, in a second step, replacing the halogen atoms with a group or mixture of groups T mentioned above.

The first step is generally carried out by the addition of the epoxides (II) and (III), successively or, preferably, simultaneously, to the phenolic compound or mixture of phenolic compounds, at a temperature of say, from 20° to 100° C. and more preferably of from 40° to 70° C., in the presence of an acid catalyst such as a Lewis acid, in particular boron trifluoride or tin tetrachloride, and, if appropriate, in the presence of a solvent, preferably a hydrocarbon or chlorohydrocarbon compound such as hexane, heptane, benzene, toluene, methylene chloride, chloroform or dichloroethane.

The phenolic compounds $R(OH)_z$ which can be used are, preferably, any monohydric or polyhydric phenol derived from benzene, naphthalene, biphenyl, diphenylmethane or 2,2-diphenylpropane, which may optionally be substituted by one or more alkyl substituents having 1 to 12 carbon atoms, and which contain a total of 6 to 18 carbon atoms.

Examples of alkyl substituents are methyl, ethyl, propyl, butyl, amyl, hexyl, octyl, nonyl, decyl, dodecyl, isopropyl, isobutyl, t.-butyl, isoamyl, isohexyl, isooctyl, isononyl, isodecyl or isododecyl groups.

The epoxides of the formula (II) are preferably 1,2-epoxyalkanes having 3 to 18 carbon atoms, alkyl glycidyl ethers of which the alkyl part R' consists of a linear or branched, saturated or unsaturated aliphatic radical containing 1 to 16 carbon atoms, or phenyl glycidyl ether.

It will be appreciated that this first step will generally result in a statiscal mixture of compounds differing in the individual values of x/z and y/z. Thus when the product is a mixture, x/z and y/z correspond to statistical average values dependent on the number of moles of the epoxides employed.

The second step of the reaction is generally carried out by heating the intermediates of the formula (IV) with mercaptoacetic, 2-mercaptopropionic or 3-mercaptopropionic acid, or with a mixture of 99 to 50% by weight of at least one of the abovementioned mercapto-acids and 1 to 50% by weight of thioethanol or thioglycerol, in the presence of an aqueous solution of NaOH or KOH and, optionally, in the presence of a solvent, preferably an alcohol of 1 to 4 carbon atoms, a glycol such as ethylene glycol, diethylene glycol or dipropylene glycol, or their corresponding ethers with $C_1$-$C_4$ alcohols, at temperatures of from 80° to 140° C.

The compounds according to the invention in which u=1 are then obtained by oxidation, preferably with hydrogen peroxide at a temperature of from 25° to 50° C.

The alkali metal halide formed is generally removed by washing with water in an acid medium or by filtration.

The compounds of formula (I) are usually in the form of a viscous liquid, paste or solid, which are generally soluble in water or dispersible in the presence of bases such as alkali metal hydroxides, aqueous ammonia or amines, in particular hydroxylated amines such as those mentioned above.

They can be used in various compositions for the care of human hair such as shampoos, rinse-off or leave-on after-shampoo products, products for more or less permanent shaping of the hair, and colouring products, in particular as foaming, wetting, dispersing, emulsifying or solubilizing agents or dyeing auxiliaries, or as carriers or excipients.

According to the intended use, they are suitably used at concentrations by weight of 0.3 to 80% of A.I. (active ingredient) and preferably of 0.5 to 30% relative to the total weight of the composition. The compositions containing the products of the invention can be, for example, aqueous or aqueous-alcoholic solutions or dispersions, pastes, gels, creams, emulsions or solids or can be presented in the form of aerosols.

Compounds of formula (I) may be used in compositions for the care of human hair in association with other constituents such as cosmetical adjuvants selected from the group comprising anionic, cationic, zwitterionic, amphoteric and non-ionic surface-active agents, anionic, cationic, non-ionic, zwitterionic and amphoteric polymers, proteins, foam synergistic agents, thickeners, opacifiers, superfatting agents, preservatives, pigments, dyestuffs, sun filters, reducing agents, oxidizing agents, solvents such as ethanol, glycols and glycol ethers, propellants such as "Freons" and electrolytes etc. The pH of these compositions is generally from 3 to 10.

This invention also provides compositions containing at least one compound or a mixture of compounds of the formula (I) and a carrier.

These compositions advantageously contain at least one compound of formula (I) and one or more cationic polymers in aqueous solution. These compositions may also contain a $C_1$ to $C_4$ alcohol or a corresponding ether of glycol or of diethylene glycol.

This invention also provides a hair treatment process which comprises applying to the hair a sufficient quantity of a composition containing one or more compounds of formula (I) and a carrier or one or more compounds of formula (I) and one or more cationic polymers.

This invention also provides a hair treatment process which comprises applying, in a first stage, a composition containing at least one cationic polymer and a carrier and, in a second stage, a composition containing at least one compound of formula (I) and a carrier, after which, if appropriate, the hair is rinsed, shaped and dried.

The compounds of formula (I) improve the foaming and/or detergent properties of the compositions and also may improve the comb-out, styling and hold of the hair.

They are generally not harsh towards the skin or towards the mucous membrane or the eye.

Compounds of formula (I) can also be used as additives in compositions for textiles, paints, varnishes and household cleaning materials, because of their foaming, detergent, wetting, dispersing, emulsifying or solubilising properties.

The invention will be further illustrated with the aid of the Examples below.

EXAMPLE 1

Preparation of a mixture of compounds of formula (I) in which:

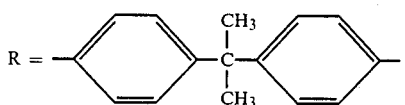

R' = C₉H₁₉
A = CH₂
T = S—CH₂—COONa
x = 2
y = 13
z = 2

(a) Preparation of the polychlorinated intermediates 22.8 g (0.1 mol) of bisphenol A are dispersed in 30 g of dichloroethane. After the addition of 0.3 ml of BF₃ etherate (catalyst), a mixture of 36.8 g (0.2 mol) of 1,2-epoxydodecane and 120.2 g (1.3 mol) of epichlorohydrin is added at 65°–70° C. over a period of 2 hours to 2 hours 30 minutes.

Two further 0.3 ml portions of catalyst are introduced during the addition of the mixture of epoxides. The reaction mixture is heated for 1 hour after the addition has ended.

After the epoxide groups have totally reacted, the dichloroethane is evaporated off under reduced pressure.

This gives a thick sticky liquid. (b) Preparation of the polyanionic polyglycerol ethers.

267 g of an aqueous solution of NaOH containing 10 meq/g are added to 124 g of thioglycolic acid (1.3 mol) under a nitrogen atmosphere. The reaction is exothermic and the termperature rises to 80° C. The previously obtained polychlorinated compounds, taken up in 80 g of methylcellosolve, are then added over a peroid of 30 minutes, after which the reaction mixture is heated for 2 hours at 100° C. The extent of reaction, determined by analysis of the remaining sulphydryl groups and measurement of the alkalinity, is greater than 93%.

The reaction mixture is diluted with 120 g of water and acidified by the addition of 240 g of 6 N hydrochloric acid.

After heating for a few minutes at 70°–75° C., the mixture is decanted and the organic phase is separated off and then washed with 300 g of water in the presence of 80 g of isopropanol.

The organic phase is evaporated under reduced pressure, water and 100 g of a 40% aqueous solution of NaOH being added so as to give an aqueous solution containing about 40% of active ingredients.

EXAMPLE 2

Preparation of a mixture of compounds of the general formula (I) in which:

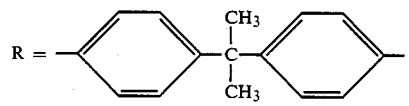

R' = C₉H₁₉
A = CH₂
T = S—CH₂—COONa
x = 1
y = 13
z = 2

The procedure is as in Example 1, starting from the following quantities of reactants:

| | |
|---|---|
| Bisphenol A | 22.8 g (0.1 mol) |
| Dichloroethane | 25 ml |
| 1,2-Epoxydodecane | 18.4 g (0.1 mol) |
| Epichlorohydrin | 129.5 g (1.4 mol) |
| BF₃ etherate | 3 × 0.3 ml |
| Methylcellosolve | 85 g |
| Thioglycolic acid | 131 g (1.4 mol) |
| Aqueous NaOH solution containing 10 meq/g | 288 g |

After adjustment of the concentration, a mixture of thiocarboxymethylated compounds of the formula (I) is obtained in the form of a yellow aqueous solution containing 40% of active ingredients, which is very slightly opalescent and has a basicity value equal to 2 meq/g.

EXAMPLE 3

Preparation of a mixture of compounds of the general formula (I) in which:

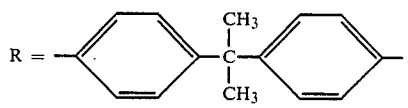

R' = C₉H₁₉
A = CH₂

T = S—CH₂—COONa
    ↓
    O x = 1
y = 13
z = 2

17.2 ml of 39% (130 volume) hydrogen peroxide are added dropwise, at between 30° and 40° C., to 100 g of the solution obtained in Example 2 (200 meq of thioether groups) to give the sulphinylcarboxylic compounds.

The solution obtained is very slightly coloured.

EXAMPLE 4

Preparation of a mixture of compounds of the general formula (I) in which:

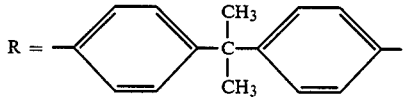

R' = C₉H₁₉
A = CH₂
T = mixture of S—CH₂—COONa and
    S—CH₂—CHOH—CH₂OH in proportions of 9/4
x = 2
y = 13
z = 2

72 g (0.52 equivalent of chlorine) of polychlorinated compounds prepared according to Example 2, solubilized in 37 g of methylcellosolve, are added in the same way to a mixture of 33.5 g of thioglycolic acid (0.36 mol), 90 g of a 40% aqueous solution of NaOH and 19 g of thioglycerol (0.16 mol).

The extent of reaction is 97% after heating for 3 hours at 100° C. After the addition of 200 g of water and 78 g of 6 N hydrochloric acid, the organic phase is separated off and then washed with 300 ml of water at 80° C. It is neutralized with 58 g of 20% NaOH solution and the resulting solution is concentrated. This finally gives 185 g of a solution containing 1.38 meq/g of COO—, that is to say 42.7% of active ingredients.

EXAMPLE 5

Preparation of a mixture of compounds of the general formula (I) in which:

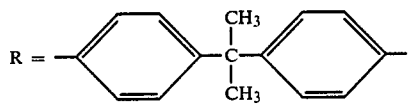

R' = C$_{13}$H$_{27}$
A = CH$_2$
T = S—CH$_2$—COONa
x = 1
y = 14
z = 2

The procedure is as in Example 1, starting from:

| Bisphenol A | 34.2 g (0.15 mol) |
|---|---|
| Dichloroethane | 40 ml |
| 1,2-Epoxyhexadecane | 36 g (0.15 mol) |
| Epichlorohydrin | 194.2 g (2.1 mol) |
| BF$_3$ etherate | 4 × 0.34 ml |
| Methylcellosolve | 125 g |
| Thioglycolic acid | 196 g |
| 40% aqueous solution of NaOH | 432 g |

This gives an aqueous solution having a basicity value equal to 2.2 meq/g, that is to say 44.8% of active ingredients, and having a slight odour which is very substantially reduced by the addition of 0.1% of glycidol.

EXAMPLE 6

Prepartion of a mixture of compounds of the formula (I) in which:

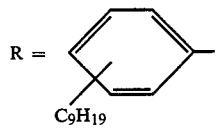

R' = C$_{12}$H$_{25}$/C$_{14}$H$_{29}$
A = CH$_2$O

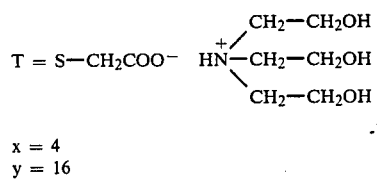

x = 4
y = 16
z = 1

(a) Preparation of the polychlorinated intermediate derivatives.

0.9 ml of boron trifluoride etherate is added to 22 g (0.1 mol) of nonylphenol, and 121 g (0.4 mol) of a mixture of dodecyl glycidyl ether and tetradecyl glycidyl ether and 148 g (1.6 mol) of epichlorohydrin are then added at 55° C. over a period of 3 hours. Stirring and heating are continued for 1 hour after the addition.

(b) Preparation of the polyanionic products.

15 g of thioglycolic acid (0.16 mol) are mixed, under a nitrogen atmosphere, with 33 g of a 40% aqueous solution of NaOH (0.33 mol), and 29 g (0.16 equivalent of chlorine of previously obtained polychlorinated compounds, diluted with 20 g of methylcellosolve (ethylene glycol monomethyl ether), are then added at 80° C. over a period of 45 minutes. The reaction mixture is then heated under reflux for 5 hours.

The mixture is acidified by the addition of 150 ml of normal hydrochloric acid. This gives a sticky white mass which is rinsed with water and subsequently taken up with 23 g of triethanolamine and then 55 g of water.

This gives an opalescent solution containing about 50% of active ingredients.

EXAMPLE 7

Preparation of a mixture of compounds of the formula (I) in which:

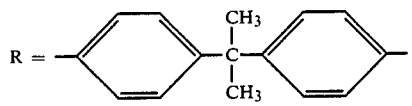

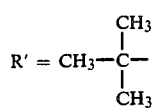

A = CH$_2$O
T = S—CH$_2$—COONa
x = 8
y = 8
z = 2

(a) Preparation of a mixture of polychlorinated compounds.

156 g (1.2 mol) of t-butyl glycidyl ether and 111 g (1.2 mol) of epichlorohydrin are mixed and added dropwise to 34.2 g (0.15 mol) of bisphenol A dispersed in 40 g of dichloroethane, in the presence of 0.9 ml of BF$_3$ etherate, at 60° C.

The reaction takes 3 hours.

The solvent is evaporated off under reduced pressure.

(b) Preparation of a mixture of polyanionic compounds.

80 g of the product thus obtained are solubilized in 40 g of methylcellosolve and added at 80° C. to 30 g of thioglycolic acid (0.32 mol) and 65 g of a 40% aqueous solution of NaOH (0.65 mol).

The reaction mixture is then heated under reflux for 4 hours.

The methylcellosolve is evaporated off and the reaction mixture is taken up with water to give a solution containing about 50% of active ingredient.

An amber-coloured solution is thus obtained which has a basicity value of 1.45 meq/g.

EXAMPLE 8

Preparation of a mixture of compounds of the formula (I) in which:

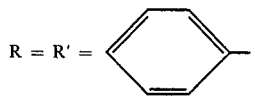

$A = CH_2O$
$x = 5$
$y = 5$
$z = 1$
$T = -S-CH_2-CH_2-COONa$ (a) Preparation of the polychlorinated intermediate derivatives.

0.65 ml of boron trifluoride etherate is added to 18.8 g (0.2 mol) of phenol, and a mixture of 150 g (1 mol) of phenyl glycidyl ether and 92.5 g (1 mol) of epichlorohydrin is then added at 60°–65° C. over a period of 2 hours. Stirring and heating are continued for 15 minutes at 70° C. after the addition.

(b) Preparation of a mixture of polyanionic products.

53 g (0.5 mol) of 3-thiopropionic acid are mixed, under a nitrogen atmosphere, with 103 g of a 40% aqueous solution of NaOH (1.03 mol), and 130.5 g (0.5 equivalent of chlorine) of previously obtained polychlorinated compounds, diluted with 65 g of methylcellosolve, are then added at between 60° and 80° C. over a period of 30 minutes. The reaction mixture is then heated at 95° C. for 4 hours.

After the addition of 100 g of water and 120 g of 6 N hydrochloric acid, the organic phase is separated off and then washed with 300 ml of water at 70° C.

The organic phase is neutralized with 160 g of 10% NaOH solution.

This gives a colourless clear solution.

APPLICATION EXAMPLES

EXAMPLE A₁

A shampoo having the following composition is prepared:
Compounds of Example 4 4.2 g
Sodium salt of sulphated alkanol ($C_{12}$–$C_{14}$) ethoxylated with 2.2 mol of ethylene oxide (containing 25% of active ingredient) 36 g
Lauric diethanolamide 1.8 g
NaOH q.s. pH 7.4 Colourant, perfume, preservative q.s. Water q.s. 100 g

EXAMPLE A₂

A shampoo having the following composition is prepared:
Compounds of Example 5 5 g
Triethanolamine alkyl($C_{12}$–$C_{14}$)-sulphate containing 40% of active ingredient 15 g
Carboxylic derivative of imidazole, an amphoteric surface-active agent sold under the name MIRANOL C 2M conc. by MIRANOL 4 g
Sodium chloride 2 g
HCl q.s. pH 6.5 Perfume, colourant, preservative q.s. Water q.s. 100 g

EXAMPLE A₃

A shampoo having the following composition is prepared:
Compounds of Example 2 3 g
Non-ionic surface-active agent of the formula: R—CHOH—CH₂—O—(CH₂CHOHCH₂O)ₙH in which R denotes a mixture of $C_9$–$C_{12}$ alkyl radicals and n represents an average statistical value of about 3.5 10 g
NaOH q.s. pH 7 Perfume, colourant, preservative q.s. Water q.s. 100 g

EXAMPLE A₄

A shampoo having the following composition is prepared:
Compounds of Example 1 4 g
Alkylglucoside at a concentration of 30% in water, sold under the name TRITON CG 110 by SEPPIC 40 g
Hydroxyethylcellulose sold under the name Natrosol 250 HHR by HERCULES 1.3 g
HCl q.s. pH 6.6 Perfume, colourant, preservative q.s. Water q.s. 100 g

EXAMPLE A₅

A shampoo having the following composition is prepared:
Compounds of Example 1 0.5 g
Polymer resulting from the condensation of diethylenetriamine and adipic acid, crosslinked with epichlorohydrin 1 g
Non-ionic surface-active agent of the formula: RCHOHCH₂O—(CH₂CHOHCH₂O)ₙH in which R denotes a mixture of $C_9$–$C_{12}$ radicals and n represents an average statistical value of about 3.5 8 g
Trideceth-7 carboxylic acid of the theoretical formula CH₃—(CH₂)₁₁CH₂—(OCH₂CH₂)₆OCH₂COOH containing 90% of active ingredient, sold under the name SANDOPAN DTC acid by SANDOZ 4 g
HCl q.s. pH 8.5 Perfume, colourant, preservative q.s. Water q.s. 100 g

EXAMPLE A₆

A shampoo having the following composition is prepared:
Compounds of Example 4 1 g
Quaternized cellulose derivative sold under the name JR 400 by UNION CARBIDE 1 g
Sodium and magnesium lauryl-ether-sulphate containing 30% of active ingredient, sold under the name TEXAPON ASV by HENKEL 30 g
Cetyldimethylamine oxide at a concentration of 30% in water, sold under the name AMMONYX CO by FRANCONYX 6 g
Sodium chloride 3 g
HCl q.s. pH 7 Perfume, colourant, preservative q.s. Water q.s. 100 g The shampoos of Examples 1 to 6 rapidly develop a copious lather. After rinsing, the hair is soft and easy to comb out.

EXAMPLE A₇

A rinse-off aerosol foam whose active principle has the following composition is prepared:
Compounds of Example 5 3 g Quaternized cellulose derivative sold under the name
Celquat L 200 by NATIONAL STARCH 1.5 g
Stearyldimethylbenzylammonium chloride 0.5 g
Sodium chloride 4 g
HCl q.s. pH 7 Perfume, colourant, preservative q.s.
Water q.s. 100 g
Aerosol packaging: Active principle of Example $A_7$
90 g
Freon 114 and Freon 12 propellant (50:50 by weight)
10 g
Total 100 g This foam is applied to cleam damp hair. After an interval of 5 to 10 minutes, the hair is rinsed. The hair is easy to comb out. Styling is easy and the hair holds its shape for a long time.

EXAMPLE $A_8$

An after-shampoo having the following composition is prepared, the weights of the constituents being expressed as active ingredients:
Compounds of Example 2 2 g
Mixture of cetylstearyl alcohol and cetylstearyl alcohol ethoxylated with 15 mol of ethylene oxide, sold under the name SINNOWAX AO by HENKEL 3 g
Hydroxyethylcellulose sold under the name CELLOSIZE QP 4400 H by UNION CARBIDE 2 g
Distearyldimethylammonium chloride 1 g
Quaternary polyvinylpyrrolidone copolymer having a molecular weight of 1,000,000, marketed under the name GAFQUAT 755 by General Aniline 1 g
NaCl 2 g
NaOH q.s. pH 7.7 Perfume, colourant, preservative, q.s. Water q.s. 100 g The same results are observed as in Example $A_7$.

EXAMPLE $A_9$

A leave-on lotion having the following composition is prepared:
Compound of Example 1 0.5 g
Polyvinylpyrrolidone copolymer having a molecular weight of 100,000, sold under the name Gafquat 734 by General Aniline 0.5 g
Water q.s. 100 g

EXAMPLE $A_{10}$

Compound of Example 6 0.5 g
Cationic silicone emulsion sold by Dow Corning under the name DC 929 0.5 g
Water q.s. 100 g

EXAMPLE $A_{11}$

Compound of Example 7 0.5 g
Monobutyl ester of poly(methyl vinyl ether/maleic anhydride), sold under the name
Gantrez ES 425 by General Aniline 0.5 g
Cationic silicone emulsion sold by Dow Corning under the name DC 929 0.5 g
Ethanol 10 g
Water q.s. 100 g The compositions of Examples $A_9$, $A_{10}$ and $A_{11}$ are applied to clean damp hair. The hair is easy to comb out and soft. When dry, the hair is soft and easy to style.

EXAMPLE $A_{12}$

Two-stage treament:
The following lotion is applied to clean damp hair:
Quaternary polyvinylpyrrolidone copolymer having a molecular weight of 100,000, sold under the name Gafquat 734 by General Aniline 0.5 g
Ethanol 10 g
Water q.s. 100 g After an interval of a few minutes, the following composition is applied:
Compound of Example 2 0.5 g
Water q.s. 100 g After an interval of a few minutes, the hair is rinsed and dried. The hair is easy to shape and comb out. The style has a good hold.

We claim:

1. A product comprising a compound of formula (I)

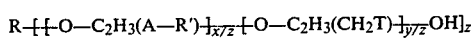

in which R denotes an aromatic or alkylaromatic radical of valency z, of 6 to 18 carbon atoms;
A denotes $CH_2$ or $CH_2$—O;
R' denotes H, an aliphatic radical having from 1 to 16 carbon atoms, or a phenyl radical, with the proviso that R' cannot denote H if A denotes $CH_2$—O;
x denotes an integer or decimal number from 1 to 8;
y denotes an integer or decimal number from 1 to 20;
z is an integer from 1 to 3; and
T denotes

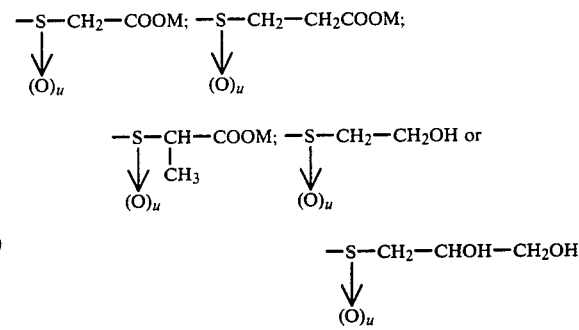

in which M denotes an alkali metal, an ammonium group or a substituted ammonium group; and
u denotes zero or 1, such that, in the product, the groups

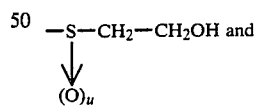 and

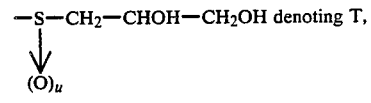 denoting T, if present, are present in a total amount of 1% to 50% by weight of the T groups.

2. A compound having the formula

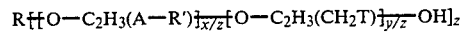

wherein
R represents an aromatic or alkylaromatic radical of valency z having 6–18 carbon atoms, A represents $CH_2$ or $CH_2$—O, R' represents hydrogen, an aliphatic radical having 1–16 carbon atoms, or a phenyl radical, with the proviso that R' cannot represent hydrogen when A represents $CH_2$—O, x represents an integer or decimal number from 1 to 8, y represents an integer or decimal number from 1 to 20, z is an integer from 1 to 3, and T represents

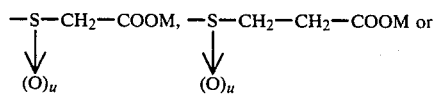

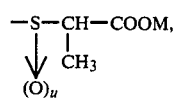

wherein M represents an alkali metal, an ammonium group or a substituted ammonium group; and u represents 0 or 1.

3. A compound having the formula

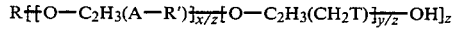

wherein

R represents an aromatic or alkylaromatic radical of valency z having 6–18 carbon atoms, A represents $CH_2$ or $CH_2$—O, R' represents an aliphatic radical having 1–16 carbon atoms, x represents an integer or decimal number from 1 to 8, y represents an integer or decimal number from 1 to 20, z is an iteger from 1–3, and T represents

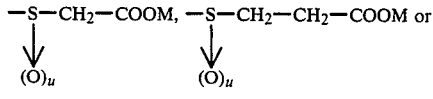

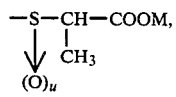

wherein M represents an alkali metal, an ammonium group or a substituted ammonium group, and u represent 0 or 1.

4. A compound having the formula

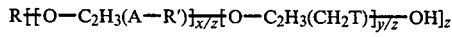

wherein

R represents an aromatic or alkylaromatic radical of valency z having 6–18 carbon atoms, A represent $CH_2$, R' represents hydrogen, an aliphatic radical having 1–16 carbon atoms, or a phenyl radical, x represents an integer or decimal number from 1 to 8;

y represents an integer or decimal number from 1 to 20;

z is an integer from 1–3, and

T represents

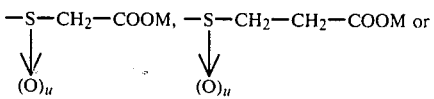

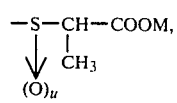

wherein M represents an alkali metal, an ammonium group or a substituted ammonium group, and u represents 0 or 1.

5. A compound having the formula

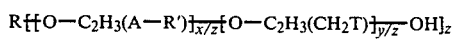

wherein

R represents an aromatic or alkylaromatic radical of valency z having 6–18 carbon atoms, A represents $CH_2$, R' represents an aliphatic radical having 1–16 carbon atoms, or a phenyl radical, x represents an integer or decimal number from 1 to 8, y represents an integer or decimal number from 1 to 20, z is an integer from 1–3, and T represents

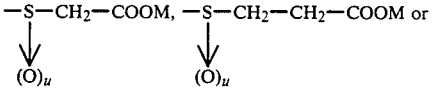

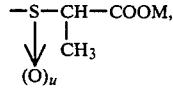

wherein M represents an alkali metal, an ammonium group or a substituted ammonium group and u represents 0 or 1.

6. The product of claim 1 wherein R represents

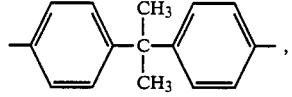

R' represent $C_9H_{19}$, A represents $CH_2$, T represents —S—$CH_2$—COONa, x=2, y=13 and x=2.

7. The product of claim 1 wherein R represents

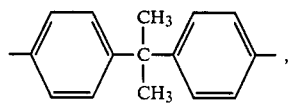

R' represents $C_9H_{19}$, A represents $CH_2$, T represents —S—$CH_2$—COONa, x=1, y=13 and z=2.

8. The product of claim 1 wherein R represents

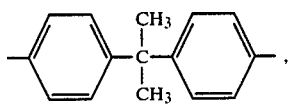

R' represent $C_9H_{19}$, A represents $CH_2$, T represents

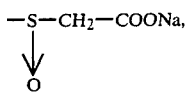

$x=1$, $y=13$ and $z=2$.

9. The product of claim 1, wherein R represents,

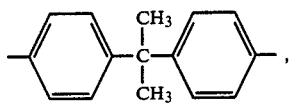

R' represents $C_9H_{19}$, A represents $CH_2$, T represents a mixture of $S-CH_2-COONa$ and $S-CH_2-CHOH\cdot CH_2OH$ in proportion of 9/4, $x=2$, $y=13$ and $z=2$.

10. The product of claim 1 wherein R represents

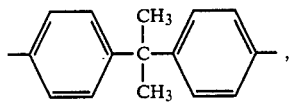

R' represents $C_{13}H_{27}$, A represents $CH_2$, T represents $-S-CH_2-COONa$, $x=1$, $y=14$ and $z=2$.

11. The product of claim 1 comprising a mixture of compounds defined by said formula (I) wherein R represents

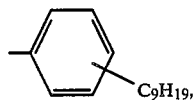

R' represents $C_{12}H_{25}$ in a portion of the compounds in said mixture and $C_{14}H_{29}$ in the remainder of the compounds in said mixture, A represents $CH_2O$, T represents $$S-CH_2COO^{\ominus}HN^{\oplus}\begin{matrix}CH_2CH_2OH\\-CH_2CH_2OH\\CH_2CH_2OH\end{matrix}$$

$x=4$, $y=16$ and $z=1$.

12. The product of claim 1 wherein R represents

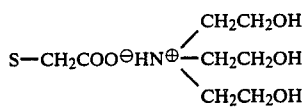

R' represents

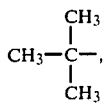

A represents $CH_2O$, T represents $S-CH_2-COONa$, $x=8$, $y=8$ and $z=2$.

13. The product of claim 1 wherein R represents

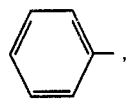

R' represents

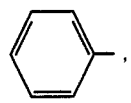

A represents $CH_2O$, T represents $-S-CH_2-CH_2-COONa$, $x=5$, $y=5$ and $z=1$.

14. A cosmetic composition comprising at least one polyanionic product as claimed in claim 1, and a carrier.

15. A composition for the care of human hair comprising at least one polyanionic product as claimed in claim 1 in the form of an aqueous or aqueous-alcoholic solution or dispersion, a paste, a gel, a crea, an emulsion, a solid or an aerosol.

16. A composition according to claim 15, wherein the concentration of the product of formula (I) is from 0.3 to 80% by weight relative to the total weight of the composition.

17. A composition according to claim 16, wherein the concentration of the product of formula (I) is from 0.5% to 30% by weight relative to the total weight of the composition.

18. A composition according to claim 16, which contains at least one adjuvant selected from the group consisting of anionic, cationic, non-ionic and amphoteric surface-active agents, anionic, cationic, non-ionic and amphoteric polymers, foam synergistic agents, proteins, thickeners, opacifiers, superfatting agents, preservatives, pigments, dyestuffs, sun filters, reducing agents, oxidizing agents, solvents, electrolytes and propellants.

19. A composition according to claim 16 which contains at least one cationic polymer.

20. A composition according to claim 15 which contains water and an alcohol of 1 to 4 carbon atoms or its glycol ether as a solvent.

21. A hair treatment process wherein a composition containing one or more compounds according to claim 1, and a carrier, or alternatively one or more compounds according to claim 1 in association with one or more cationic polymers, is applied to the hair.

22. A two-stage hair treatment process, wherein in a first stage, a composition containing at least one cationic polymer and a carrier is applied, and, in a second stage, a composition according to claim 15 is applied to the hair, after which the hair is rinsed and/or shaped and then dried.

* * * * *